United States Patent
Vitek et al.

(10) Patent No.: US 6,419,648 B1
(45) Date of Patent: Jul. 16, 2002

(54) SYSTEMS AND METHODS FOR REDUCING SECONDARY HOT SPOTS IN A PHASED ARRAY FOCUSED ULTRASOUND SYSTEM

(75) Inventors: Shuki Vitek; Naama Brenner, both of Haifa (IL)

(73) Assignee: Insightec-TxSonics Ltd., Tirat Carmel (IL)

( * ) Notice: Subject to any disclaimer, the term of this patent is extended or adjusted under 35 U.S.C. 154(b) by 0 days.

(21) Appl. No.: 09/556,095

(22) Filed: Apr. 21, 2000

(51) Int. Cl.$^7$ ................................................ A61N 7/02
(52) U.S. Cl. ............................................ 601/3; 606/27
(58) Field of Search ................................ 600/437, 439; 601/2, 3, 4; 604/22; 606/27

(56) References Cited

U.S. PATENT DOCUMENTS

| | | |
|---|---|---|
| 4,441,486 A | 4/1984 | Pounds |
| 4,549,533 A | 10/1985 | Cain et al. |
| 4,586,512 A | 5/1986 | Do-huu et al. |
| 4,858,597 A | 8/1989 | Kurtze et al. |
| 4,865,042 A | 9/1989 | Umemura et al. |
| 4,888,746 A | 12/1989 | Wurster et al. |
| 5,247,935 A | 9/1993 | Cline et al. |
| 5,275,165 A | 1/1994 | Ettinger et al. |
| 5,291,890 A | 3/1994 | Cline et al. |
| 5,307,812 A | 5/1994 | Hardy et al. |
| 5,323,779 A | 6/1994 | Hardy et al. |
| 5,327,884 A | 7/1994 | Hardy et al. |
| 5,368,031 A | 11/1994 | Cline et al. |
| 5,368,032 A | 11/1994 | Cline et al. |
| 5,435,304 A * | 7/1995 | Oppelt et al. ............... 600/439 |
| 5,443,068 A | 8/1995 | Cline et al. |
| 5,490,840 A | 2/1996 | Uzgiris et al. |
| 5,501,655 A * | 3/1996 | Rolt et al. ...................... 601/3 |
| 5,507,790 A | 4/1996 | Weiss |
| 5,520,188 A | 5/1996 | Hennige et al. |
| 5,526,814 A | 6/1996 | Cline et al. |
| 5,526,815 A * | 6/1996 | Granz et al. ................. 600/439 |
| 5,573,497 A | 11/1996 | Chapelon |
| 5,590,657 A | 1/1997 | Cain et al. |

(List continued on next page.)

OTHER PUBLICATIONS

Charles A. Cain, et al., "Concentric–Ring and Sector–Vortex Phased–Array Applicators for Ultrasound Hyperthermia", IEEE Transactions on Microwave Theory and Techniques, MTT–34, pp. 542–551, 1986.

Todd Fjield, et al., "The Combined Concentric–Ring and Sector–Vortex Phased Array for MRI Guided Ultrasound Surgery", IEEE Transactions on Ultrasonics, Ferroelectircs and Frequency Control, vol. 44, No. 5, pp. 1157–1167, Sep. 1997.

Nathan McDannold, et al., "MRI Evaluation of Thermal Ablation of Tumors and Focused Ultrasound", JMRI vol. 8, No. 1, pp. 91–100, Jan/Feb. 1998.

Lufkin, Robert B., "Interventional MRI," Mosby (1999), Chapter 25, pp. 237–243.

Harvey E. Cline, Ph.D., et al., "Focused US System for MR Imaging–Guide Tumor Ablation", Radiology vol. 194, No. 3, pp. 731–738, Mar. 1995.

Primary Examiner—Shawna J. Shaw
(74) Attorney, Agent, or Firm—Lyon & Lyon LLP

(57) ABSTRACT

System and methods for performing a therapeutic procedure using focused ultrasound include providing a piezoelectric transducer including a plurality of transducer elements, such as a concave concentric ring array or a liner array of transducer elements. Drive circuitry is coupled to the transducer for providing drive signals to the transducer elements at one of a plurality of discrete RF frequencies. A controller is coupled to the drive circuitry for periodically changing a frequency of the drive signals to one of the plurality of discrete frequencies, while controlling a phase component of the drive signals to maintain the focus of the transducer at a primary focal zone during a single sonication.

25 Claims, 2 Drawing Sheets

U.S. PATENT DOCUMENTS

| | | |
|---|---|---|
| 5,665,054 A | 9/1997 | Dory |
| 5,694,936 A * | 12/1997 | Fujimoto et al. ........... 600/439 |
| 5,711,300 A | 1/1998 | Schneider et al. |
| 5,743,863 A | 4/1998 | Chapelon |
| 5,769,790 A | 6/1998 | Watkins et al. |
| 5,823,962 A * | 10/1998 | Schaetzle et al. ........... 600/439 |
| 5,873,845 A | 2/1999 | Cline et al. |
| 6,042,556 A * | 3/2000 | Beach et al. .................... 601/3 |
| 6,267,734 B1 * | 7/2001 | Ishibashi et al. ................ 601/2 |

* cited by examiner

SYSTEMS AND METHODS FOR REDUCING SECONDARY HOT SPOTS IN A PHASED ARRAY FOCUSED ULTRASOUND SYSTEM

FIELD OF THE INVENTION

The present invention relates generally to systems and methods for performing noninvasive surgical procedures using focused ultrasound, and more particularly to systems and methods for reducing secondary hot spots created by a focused ultrasound transducer array.

BACKGROUND

High intensity focused acoustic waves, such as ultrasonic waves (acoustic waves with a frequency greater than about 20 kilohertz), may be used to therapeutically treat internal tissue regions within a patient. For example, ultrasonic waves may be used to ablate tumors, thereby obviating the need for invasive surgery. For this purpose, piezoelectric transducers driven by electric signals to produce ultrasonic energy have been suggested that may be placed external to the patient but in close proximity to the tissue to be ablated. The transducer is geometrically shaped and positioned such that the ultrasonic energy is focused at a "focal zone" corresponding to a target tissue region within the patient, heating the target tissue region until the tissue is necrosed. The transducer may be sequentially focused and activated at a number of focal zones in close proximity to one another. This series of sonications is used to cause coagulation necrosis of an entire tissue structure, such as a tumor, of a desired size and shape.

A spherical cap transducer array, such as that disclosed in U.S. Pat. No. 4,865,042 issued to Umemura et al., has been suggested for this purpose. This spherical cap transducer array includes a plurality of concentric rings disposed on a curved surface having a radius of curvature defining a portion of a sphere. The concentric rings generally have equal surface areas and may also be divided circumferentially into a plurality of curved transducer elements or sectors, creating a sector-vortex array. The transducer elements are driven by radio frequency (RF) electrical signals at a single frequency offset in phase and amplitude. In particular, the phase and amplitude of the respective drive signals may be controlled so as to focus the emitted ultrasonic energy at a desired "focal distance," i.e., the distance from the transducer to the center of the focal zone and provide a desired energy level in the target tissue region.

Although the transducer elements are focused at a desired primary focal zone, there may also be one or more secondary focal zones at locations other than the intended primary focal zone. For example, spaces between the concentric rings may contribute to such "hot spots," particularly in the "near field," i.e., the region between the transducer and the primary focal zone. Such secondary hot spots may lead to undesired heating, pain for the patient, and/or possibly necrosis of tissue in the near field. Because the transducer is made up of a finite number of rings, the step function used to change the phase between the rings may also contribute to the creation of secondary hot spots.

To minimize the effects of secondary hot spots, one proposed solution has been to use a wide-band frequency signal to drive the transducer elements, such that the location of the secondary hot spots may be "smeared" by this wide-band signal, i.e., the energy diffused within tissue regions at different locations within the patient, thereby reducing the risk of heating the tissue regions sufficiently to necrose them. This solution, however, may be limited by the transducer bandwidth and may require special complicated electronics. Wide-band drive signals may also smear the primary focal zone, thereby requiring increased ultrasonic energy delivery to ablate the target tissue at the primary focal zone. The smearing of the primary focal zone may be at least partially corrected by introducing appropriate delays in the signals, but this may substantially complicate control of the phased array, for example, requiring additional electronic phasing and focusing.

Accordingly, it would be desirable to provide systems and methods for treating a tissue region using ultrasound energy at one or several discrete frequencies that reduces secondary hot spots, without substantially reducing the intensity at the Be primary focal zone.

SUMMARY OF THE INVENTION

The present invention is directed to systems and methods for performing a therapeutic procedure using focused ultrasound that substantially minimizes the effects of secondary hot spots, without adversely impacting on the energy delivered to the primary focal zone.

In a preferred embodiment, a focused ultrasound system includes a transducer formed from piezoelectric material that includes a plurality of transducer elements. The transducer elements may be provided in a variety of arrays or geometries. For example, in one exemplary embodiment, the transducer may be a substantially concave phased array, including a plurality of concentric rings. Each transducer ring may be divided circumferentially into a plurality of curved elements or "sectors." Alternatively, a linear array of transducer elements may be provided. Other arrangements or geometries of transducer elements may also be provided, such as a checkerboard pattern, a hexagonal lattice, or a random pattern of transducer elements, and the invention should not be limited to any one particular geometry.

Drive circuitry is coupled to each of the respective transducer elements for providing drive signals to each transducer element at one of a plurality of discrete frequencies, preferably at radio frequencies. A controller is coupled to the drive circuitry for periodically changing a frequency of the drive signals during a single sonication between one of the plurality of discrete frequencies. In particular, the controller determines a phase component for each of the respective drive signals provided, such that a primary focal zone of a given size and shape results at a predetermined distance from the transducer.

The transducer is preferably adjustably mounted within a casing, such as a fluid-filled table, onto which a patient may be disposed. During use of the system, the plurality of transducer elements may be activated with a set of drive signals, each at a single frequency, while focusing ultrasonic energy produced by the transducer elements at the primary focal zone, corresponding to the location of a target tissue region in a patient. Periodically, the frequency of the respective drive signals may be changed, while substantially maintaining the focus at the primary focal zone. Preferably, this is achieved by controlling the phase component of the drive signals when the frequency of the drive signals is changed.

The series of drive signals is provided to the transducer to create a single sonication that substantially ablates the tissue at the target tissue region, while minimizing the effects of secondary focal zones or "hot spots." As the frequency is changed, the location of the secondary hot spots may change, thereby dispersing the ultrasonic energy at the secondary hot spots to several locations within the patient's body. Thus, while the target tissue region receives sufficient energy to substantially necrose the tissue there, the tissues at the secondary hot spots do not.

Other objects and features of the present invention will become apparent from consideration of the following description taken in conjunction with the accompanying drawings.

BRIEF DESCRIPTION OF THE DRAWINGS

Preferred embodiments of the present invention are illustrated by way of example, and not by way of limitation, in the figures of the accompanying drawings, in which like reference numerals refer to like components, and in which.

DETAILED DESCRIPTION OF THE PREFERRED EMBODIMENTS

Figure 1A:
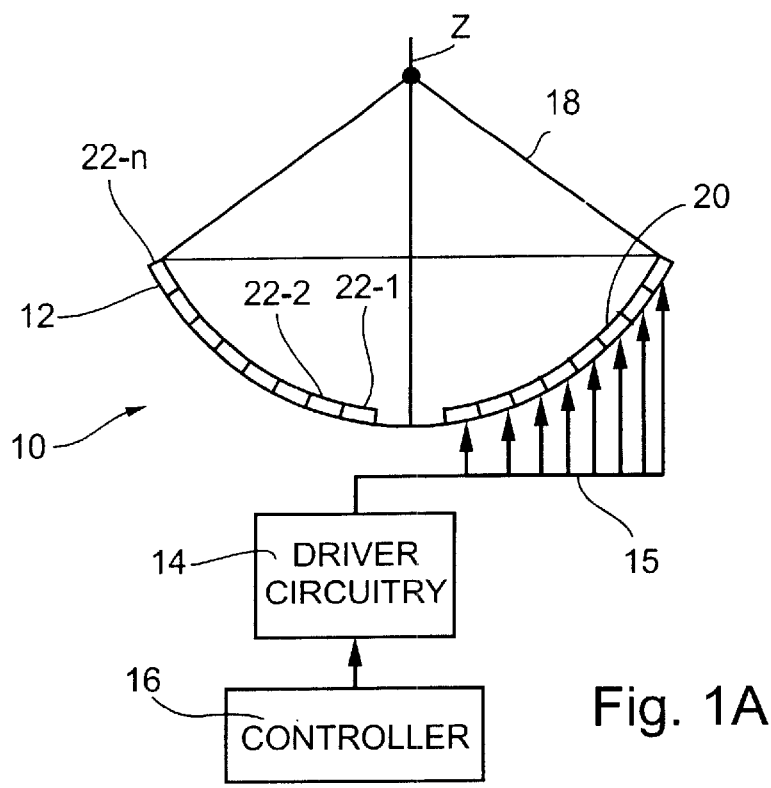
FIG. 1A is a schematic diagram of one embodiment of a focused ultrasound system, in accordance with the present invention.
Figure 1B:
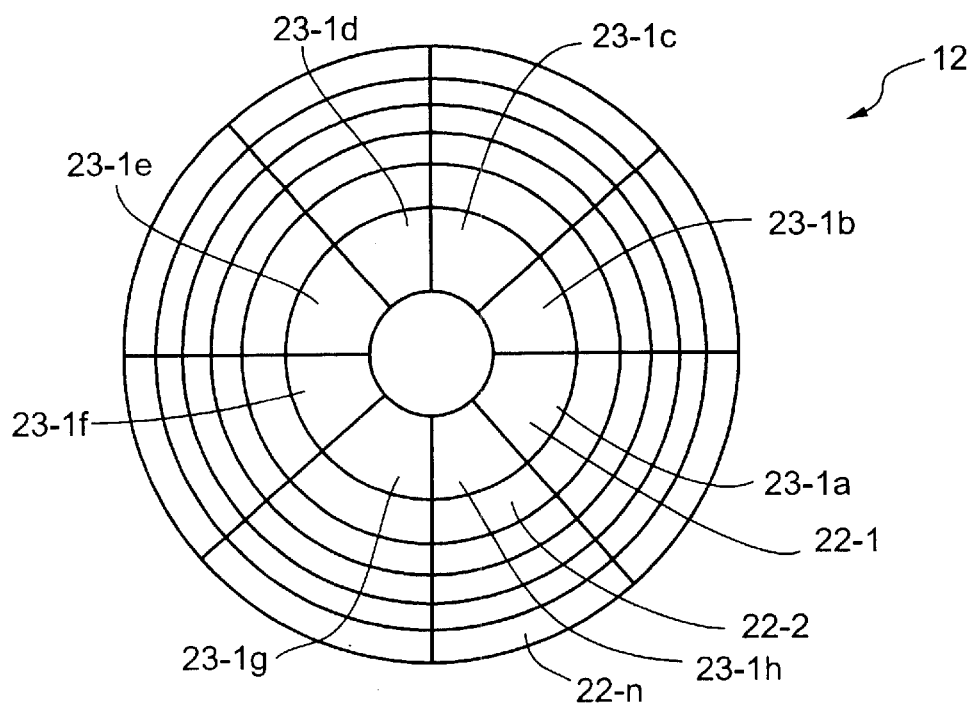
FIG. 1B is a top view of the transducer array of the focused ultrasound system of FIG. 1A.
Figure 2:
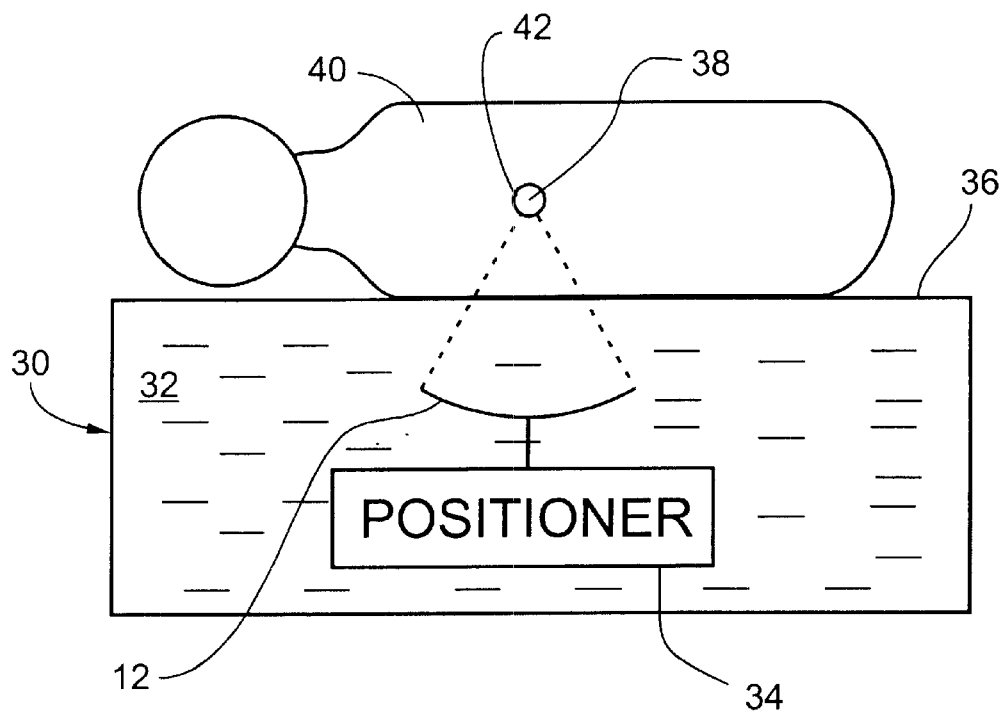
FIG. 2 is a schematic side view of a patient on a water-filled table having an ultrasound transducer array therein.

Turning now to the drawings, FIGS. 1A, 1B, and 2 show a preferred embodiment of a system 10 for performing a therapeutic procedure using focused ultrasound, in accordance with the present invention. The system 10 generally includes a transducer 12, drive circuitry 14 for providing electrical drive signals 15 to the transducer 12, and a controller 16 for controlling the drive signals 15 provided by the drive circuitry 14. The transducer 12 is preferably a phased array ultrasound transducer formed from piezoelectric material, constructed as is known to those skilled in the art.

In one preferred embodiment, shown in FIGS. 1A and 1B, the transducer 12 may have a concave or bowl shape, such as a "spherical cap" shape, i.e., having a substantially constant radius of curvature 18 such that the transducer 12 has an inside surface 20 defining a portion of a sphere. The transducer 12 may be divided into a plurality of concentric rings 22-1 to 22-n (where n is the total number of rings), for example, by cutting concentric circles through a piezoelectric shell (not shown). Preferably, each of the rings 22-1 to 22-n has substantially the same surface area, and thus, the widths of the rings 22 are progressively smaller from the innermost ring 22-1 outward to the outermost ring 22-n. Alternatively, the rings 22 may have equal widths (not shown), such that the area of each ring 22 is progressively larger from the innermost ring to the outermost ring. Any spaces (not shown) between the rings 22 may be filled with silicone rubber and the like to substantially isolate the rings 22 from one another. Each ring 22 may also be divided circumferentially into curved elements or "sectors" 23 (23-1a to 23-1h are illustratively shown for the innermost ring 22-1 in FIG. 1B), for example, by removing thin radial strips of electrode (not shown) from the back of the transducer 12 between each sector 23. In a preferred embodiment, the transducer 12 has an outer diameter of between about 8–12 cm, a radius of curvature 18 between about 8–6 cm, and includes between about ten and thirty rings 22, each of which is divided into 4–16 sectors 23.

Additional information on the construction of a phased array transducer appropriate for use with the present invention may be found, for example, in T. Fjield and K. Hynynen, "The Combined Concentric-Ring and Sector-Vortex Phased Array for MRI Guided Ultrasound Surgery," IEEE Transactions on Ultrasonics, Ferroelectrics, and Frequency Control, vol. 44, no. 5, pages 1157–1167 (September. 1997), the disclosure of which is expressly incorporated herein by reference. Alternatively, a concentric-ring transducer may be provided that is not divided into circumferential sectors (not shown). Such a concentric-ring transducer is shown, for example, in C. Cain and S. Umemura, "Concentric-Ring and Sector-Vortex Phased-Array Applicators for Ultrasound Hyperthermia," IEEE Transactions on Microwave Theory and Techniques, vol. MTT-34, no. 5, pages 542–551 (May 1986), the disclosure of which is expressly incorporated herein by reference.

In another preferred embodiment (not shown), a linear array of transducer elements may be provided that may be focused at a primary focal zone having a desired shape, such as a linear focal zone. Alternatively, other arrangements or geometries of transducer elements may be provided, such as a checkerboard pattern or a hexagonal lattice. The transducer elements may be provided on a curved, spherical cap transducer, a substantially flat transducer, and the like, that may be focused at a primary focal zone.

Returning to FIG. 1B, each of the sectors 23 of the rings 22 is individually coupled to the drive circuitry 14 in a conventional manner. The drive circuitry 14 is configured to provide electrical drive signals 15 to the sectors 23 at a plurality of discrete frequencies, preferably at radio frequencies (RF), for example, between about 0.5–10 MHz, and more preferably between about 1.0 and 2.0 MHz. When electrical drive signals 15 are provided to the sectors 23, the transducer 12 emits ultrasonic energy from its inside surface 20, as is known to those skilled in the art.

The controller 16 is coupled to the drive circuitry 14 for controlling several aspects of the drive signals 15 generated by the drive circuitry 14, such as the frequency, phase, and amplitude. First, the controller 16 may control the amplitude of g the drive signals 15, for example, to control the intensity of ultrasonic energy delivered by the transducer 12. In addition, the controller 16 may control the phase between each of the concentric rings 22 and between each of the sectors 23. By shifting the phase between the concentric rings 22, a "focal distance," i.e., the distance from the transducer 12 to the center of the focal zone, may be adjusted along the z axis, as is know to those skilled in the art.

Shifting the phase between the sectors 23 allows control of the size and shape of the focal zone of the ultrasonic energy, or "mode" of the transducer 12, as is also known to those skilled in the art. Further information on phase shifting of phased array transducers may be found in the Fjield and Cain articles referenced above, as well as in U.S. Pat. No. 4,865,042 issued to Umemura et al., the disclosure of which is also expressly incorporated herein by reference.

The controller 16 also preferably controls the frequency of the drive signals 15 provided to the transducer 12. The drive signals 15 supplied to the transducer 12 at one time are all preferably provided at the same discrete frequency. During a single sonication, which may have a duration of between about 5–20 seconds, and more preferably about 10 seconds or more, the controller 16 may periodically change the frequency of the drive signals 15, for example, at most once every second, and preferably as often as about every 0.2–0.5 seconds. At the same time, the controller 16 controls the phase and/or amplitude of the drive signals 15 to maintain the focal zone of the resulting ultrasonic energy generated by the transducer 12 at a desired region within a patient's body. Thus, the controller 16 may direct the drive circuitry to provide a plurality of sequential sets of drive signals 15, each set being at a discrete frequency different from the previous set.

As shown in FIG. 2, the transducer 12 is preferably mounted within a fluid-filled casing, such as table 30. The table 30 includes a chamber 32 filled with degassed water or similar acoustically transmitting fluid. The transducer 12 is preferably connected to a positioning system 34 that moves the transducer 12 within the chamber 32, and consequently mechanically adjusts the focal zone 38 of the transducer 12. For example, the positioning system 34 may be configured to move the transducer 12 within the chamber 32 in any one of three orthogonal directions, e.g., horizontally forward and backward, horizontally side-to-side, and vertically. U.S. Pat. Nos. 5,247,935 issued to Cline et al. and 5,275,165 issued to Ettinger et al., the disclosures of which are expressly incorporated herein by reference, disclose exemplary positioning systems that may be used.

Alternatively, the positioning system 34 may simply pivot the transducer 12 about a fixed point within the chamber 45, i.e., to change the angle of the transducer 12 and consequently the focal zone 38 with respect to a horizontal plane (not shown). In this alternative, the focal distance of the transducer 12 may be controlled electronically by changing the phase and/or amplitude of the drive signals 15 provided to the transducer 12, as described above. In further alternatives, the positioning system 34 may move the transducer 12 in a horizontal plane perpendicular to the line of propagation (not shown), with the depth controlled electronically, or other combinations of mechanical and electronic positioning may be used.

The top of the table 30 includes a flexible membrane 36 that is substantially transparent to ultrasound, such as a mylar plastic or polyvinyl chloride (PVC) sheet. A fluid-filled bag or cushion is generally provided along the top of the table that may conform easily to the contours of a patient placed on the table. In a further alternative, the transducer 10 may be mounted in a fluid-filled bag mounted on a movable arm (not shown) that may be placed in contact with a patient, such as that disclosed in U.S. Pat. No. 5,526,814, the disclosure of which is expressly incorporated herein by reference.

In addition, the system 10 may include an imaging device (not shown) for monitoring the use of the system during treatment of a patient. For example, the system 10 may be placed within a magnetic resonance imaging (MRI) device, such as that disclosed in U.S. Pat. Nos. 5,247,935, 5,291,890, 5,368,031, 5,368,032, 5,443,068 issued to Cline et al., and U.S. Pat. Nos. 5,307,812, 5,323,779, 5,327,884 issued to Hardy et al., the disclosures of which are expressly incorporated herein by reference.

Returning to FIG. 2, during use, a patient 40 may be disposed on the table 30 with water, ultrasonic conducting gel, and the like applied between the patient 30 and the bag or membrane 36, thereby acoustically coupling the patient 30 to the transducer 12. The transducer 12 may be focused towards a target tissue region within a tissue structure 42, which may, for example, be a cancerous or benign tumor. The transducer 12 may be activated by supplying a set of drive signals 15 at a discrete frequency to the transducer 12 to focus ultrasonic energy at the target tissue region 42. During the course of the sonication, the frequency of the drive signals 15 may be changed periodically, as described above, while maintaining the focus at the target tissue region 42. The transducer 12 may be activated for sufficient time to substantially necrose the target tissue region 42, e.g., between about 5–20 seconds, and more preferably about 10 seconds or more.

The transducer 12 may be deactivated, for example, for sufficient time to allow heat absorbed by the patient's tissue to dissipate, e.g., between about 45–90 seconds, and more preferably about 60 seconds or more. The transducer 12 may then be focused on another target tissue region (not shown), for example, adjacent to the target tissue region 42, and the process repeated until the entire target tissue structure is ablated.

A system in accordance with the present invention uses control of the frequency of the drive signals, preferably during a single substantially continuous sonication, to reduce the effects of secondary hot spots. Because the locations of both primary and secondary focal zones vary depending upon the frequency of the drive signals, different frequency drive signals may cause the focal zones or "hot spots" created by the transducer to move to different locations or focal distances within the patient as the frequency is changed. The controller of a system according to the present invention changes the frequency, but substantially maintains the primary focal zone of the ultrasonic energy at a target region within a patient's body by simultaneously adjusting the phase and/or amplitude of the drive signals provided to the transducer elements. The secondary hot spots, however, do not remain at the same locations, but become focused at different locations as the frequency is changed.

Figure 3:
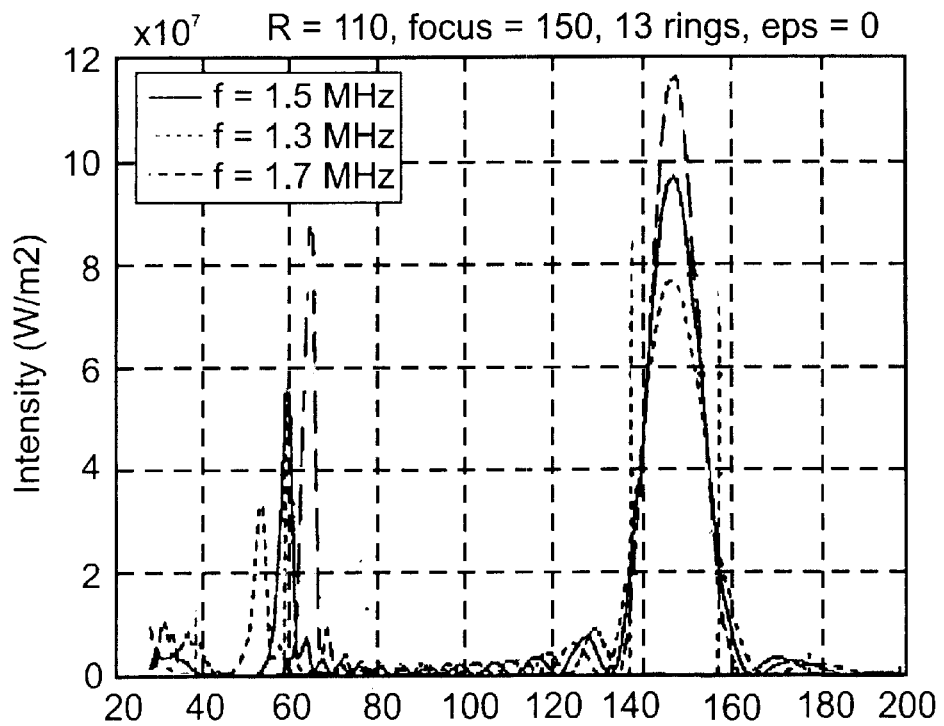
FIG. 3 is a graph showing the locations of secondary hot spots for various frequency signals used to drive an ultrasound transducer focused at a fixed primary focal zone.

This is illustrated, for example, in FIG. 3, which shows the energy intensity (in $W/m^2$) produced by a transducer in relation to the distance (z) from the transducer. In this example, the transducer is focused at a focal distance of about 150 mm, while the frequency of the drive signals is changed from 1.3 MHz, to 1.5 MHz, to 1.7 MHz. As may be seen from the three corresponding curves, the distances from the transducer of the secondary hot spots shift from about 55 mm at 1.3 MHz, to about 60 mm at 1.5 MHz, to about 65 mm at 1.7 MHz. Thus, the energy delivered at the secondary hot spots is absorbed by different tissue regions as the frequency changes. This diffuses the energy, substantially minimizing the risk of heating tissue at the secondary hot spots to an intensity level sufficient to cause pain, or damage or necrose the tissue. Because the primary focal zone remains substantially constant at a fixed focal distance, the tissue at the primary focal zone may be heated sufficiently to achieve necrosis.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

What is claimed is:

1. A system for performing a therapeutic procedure in a target tissue region of a patient using focused ultrasound within a primary focal zone, comprising:

an array of transducer elements;

drive circuitry coupled to the transducer elements, the drive circuitry configured to provide respective drive signals to the transducer elements of at least first, second, and third discrete frequencies; and a controller coupled to the drive circuitry, the controller configured for periodically changing the frequency of the respective drive signals provided by the drive circuitry between at least the first, second, and third frequencies while substantially maintaining focus at the primary focal zone during a single, substantially continuous, sonication, the controller changing the frequency less than once every 50 milliseconds.

2. The system of claim 1, wherein the controller is further configured for controlling a phase component of the respective drive signals to focus the transducer elements substantially at the primary focal zone at the firsts second and third frequencies.

3. A method for performing a therapeutic procedure in a target tissue region of a patient using focused ultrasound, the method comprising:

driving a plurality of transducer elements with a set of respective drive signals at a first discrete frequency, while focusing ultrasonic energy produced by the transducer elements at a primary focal zone within the target tissue region and creating a secondary focal zone at a location outside the primary focal zone; and changing the frequency of the respective drive signals to a second discrete frequency, while substantially maintaining the focus at the primary focal zone and moving the secondary focal zone to another location outside the primary focal zone; wherein the frequency is changed less than once every 50 ms.

4. The method of claim 3, wherein each drive signal has a respective phase component, and wherein the respective phase components of the drive signals are controlled when the frequency of the respective drive signals is changed, in order to substantially maintain the focus at the primary focal zone.

5. The method of claim 3, wherein the transducer elements comprise a concentric ring array divided circumferentially into a plurality of curved elements, and wherein a phase component of the respective drive signals driving each of the curved elements is controlled to provide a desired size and shape of the primary focal zone.

6. The method of claim 3, wherein the step of changing the frequency comprises alternating the frequency of the respective drive signals between a fixed set of frequencies comprising the first and second frequencies during a single sonication.

7. The method of claim 6, wherein the fixed set of frequencies includes one or more additional frequencies in addition to the first and second frequencies, and wherein the frequency of the respective drive signals is alternated in a predetermined sequence.

8. The method of claim 6, wherein the frequency of the respective drive signals is alternated between the fixed set of frequencies no more than once every 0.2 second.

9. The method of claim 8, wherein the frequency of the respective drive signals is alternated between the fixed set of frequencies at most once every second.

10. The method of claim 8, wherein the frequency of the respective drive signals is alternated between the fixed set of frequencies every 0.2–0.5 second.

11. The method of claim 6, wherein the sonication has a duration of about ten (10) seconds or more.

12. The method of claim 6, wherein the sonication having a duration of between about 5–20 seconds.

13. The method of claim 6, wherein the frequency of the respective drive signals is alternated between the fixed set of frequencies no more than 10–100 times during a single sonication.

14. A method for performing a therapeutic procedure in a target tissue region of a patient using focused ultrasound, the method comprising:

driving a plurality of transducer elements with a first set of respective drive signals at a first frequency for longer than 50 ms, while focusing ultrasonic energy produced by the transducer elements substantially at a primary focal zone within the target tissue region and creating a secondary focal zone outside the primary focal zone; and driving the plurality of transducer elements with a second set of respective drive signals at a second frequency for longer than 50 ms, while maintaining the focus of the ultrasonic energy produced by the transducer elements substantially at the primary focal zone and moving the secondary focal zone to another location outside the primary focal zone.

15. The method of claim 14, wherein the ultrasonic energy of the transducer elements is focused at the primary focal zone by controlling a phase component of the respective drive signals.

16. The method of claim 14, wherein the transducer elements comprise a concentric ring array divided circumferentially into a plurality of curved elements, and wherein a phase component of the respective drive signals driving each of the curved elements is controlled to provide a desired size and shape of the primary focal zone.

17. The method of claim 14, comprising the additional step of driving the plurality of transducer elements with a third set of respective drive signals at a third frequency, while maintaining the focus of the ultrasonic energy produced by the transducer elements substantially at the primary focal zone.

18. A system for performing a therapeutic procedure in a target tissue region of a patient using focused ultrasound within a primary focal zone, comprising:

an array of transducer elements;

drive circuitry coupled to the transducer elements, the drive circuitry configured to provide respective drive signals to the transducer elements of at least first and second discrete frequencies; and a controller coupled to the drive circuitry for periodically changing the frequency of the respective drive signals provided by the drive circuitry between at least the first and second frequencies while substantially maintaining focus at the primary focal zone, the controller maintaining the respective drive signals at the first frequency for at least 0.2 second before changing the respective drive signals to the second frequency.

19. The system of claim 18, wherein the controller is configured for changing the frequency of the respective drive signals at most once every second during a single sonication.

20. The system of claim 19, wherein the controller is configured for changing the frequency of the respective drive signals every 0.2–0.5 second signals during a single sonication.

21. The system of claim 18, wherein the controller is configured for periodically changing the frequency of the respective drive signals between a plurality of discrete frequencies in a predetermined sequence during a single sonication having a duration of about ten (10) seconds or more.

22. The system of claim 18, wherein the controller is configured for periodically changing the frequency of the respective drive signals between a plurality of discrete frequencies in a predetermined sequence during a single, substantially continuous sonication having a duration of between about 5–20 seconds.

23. The system of claim 18, wherein the controller is further configured for controlling a phase component of the respective drive signals to focus the transducer elements substantially at a primary focal zone at the first and second frequencies, while changing a location of a secondary focal zone outside the primary focal zone.

24. The system of claim 18, wherein the controller is configured for maintaining the respective drive signals at the second frequency for at least 0.2 second before changing the frequency of the respective drive signals.

25. The system of claim 18, wherein the controller is configured for changing the frequency of the respective drive signals no more than 10–100 times during a single sonication.

* * * * *